United States Patent [19]

Tanaka et al.

[11] 4,059,686

[45] Nov. 22, 1977

[54] PHARMACEUTICAL PREPARATION FOR ORAL CAVITY ADMINISTRATION

[75] Inventors: Wataru Tanaka, Hoya; Eiichiro Akito, Omiya; Koichi Yoshida, Soka; Takashi Terada, Yono; Hiroshi Ninomiya, Sayama, all of Japan

[73] Assignee: Nippon Kayaku Kabushiki Kaisha, Tokyo, Japan

[21] Appl. No.: 615,301

[22] Filed: Sept. 22, 1975

[30] Foreign Application Priority Data

Sept. 24, 1974 Japan .................................. 49-108891

[51] Int. Cl.$^2$ ...................... A61K 9/22; A61K 31/78; A61K 31/45; A61K 9/26

[52] U.S. Cl. ........................................ 424/19; 424/81; 424/83; 424/22

[58] Field of Search ....................... 424/19, 81, 83, 22; 426/19, 549, 601

[56] References Cited

U.S. PATENT DOCUMENTS

| | | | |
|---|---|---|---|
| 2,987,445 | 6/1961 | Levesque et al. | 424/81 |
| 3,029,188 | 4/1962 | Cyr et al. | 424/83 |
| 3,147,187 | 9/1964 | Playfair | 424/19 |
| 3,911,099 | 10/1975 | DeFoney et al. | 424/22 |

FOREIGN PATENT DOCUMENTS

| | | | |
|---|---|---|---|
| 2,017,409 | 10/1971 | Germany | 424/81 |
| 1,233,055 | 6/1968 | United Kingdom | 424/19 |

OTHER PUBLICATIONS

Siegele et al., "Coagulation of Oil-Extended Emulsions," Chem. Abstracts, vol. 83, 1975, parag. 80034v.

*Primary Examiner*—Henry R. Jiles
*Assistant Examiner*—Cary Owens
*Attorney, Agent, or Firm*—Schuyler, Birch, Swindler, McKie & Beckett

[57] ABSTRACT

A pharmaceutical preparation of oral cavity administration, characterized by being a mixture of a pharmacologically active agent, a pharmaceutical carrier, and sodium polyacrylate, in conventional dosage form. It has advantages in that it adheres strongly to local site and dissolves gradually over a prolonged period of time while releasing appropriate amounts of the active agent.

8 Claims, 3 Drawing Figures

PHARMACEUTICAL PREPARATION FOR ORAL CAVITY ADMINISTRATION

This invention relates to a pharmaceutical preparation for oral cavity administration and to a method of making same. More particularly, it relates to a pharmaceutical preparation for oral cavity administration with superior adhesion to local sites, characterized by being a mixture of a pharmacologically active agent, a pharmaceutical carrier, and sodium polyacrylate (hereinafter referred to as PANA), in usual dosage form, and to a method of making same.

Among pharmaceutical preparations for oral cavity administration, there have heretofore been known buccal tablets, sublingual tablets, ointments, etc. The buccal tablet and sublingual tablet currently available on the market have a defect of giving to the patients an impulse to crunch and swallow the tablet because of the feeling of foreign body imparted by it. Such a tablet, moreover, is very difficult to be held in the mouth for a long period of time. There has been known, on the other hand, an ointment imparted with stickiness and a suitable degree of affinity to a wet site by kneading a greasy base together with gelatin, carboxymethylcellulose, or the like, but this ointment is not yet satisfactory for oral cavity administration because of its insufficient adhesion and rather high solubility.

The above-mentioned defects were found to be overcome by incorporating an adequate amount of PANA into a preparation for oral cavity administration in accordance with this invention, whereby the resulting preparation becomes strongly adherent to local site and dissolves gradually over a long period of time while releasing appropriate amounts of the active component.

It is possible to obtain pharmaceutical preparations for oral cavity administration such as buccal tablets, sublingual tablets, and ointments by mixing a medicinal agent, a pharmaceutical carrier, and sodium polyacrylate and making the resulting mixture into a preparation in conventional manner. The resulting preparation is superior to a customary preparation in that it adheres strongly to oral mucous membrane and the medicinal agent is gradually released and absorbed.

In the accompanying drawings.

Figure 1:
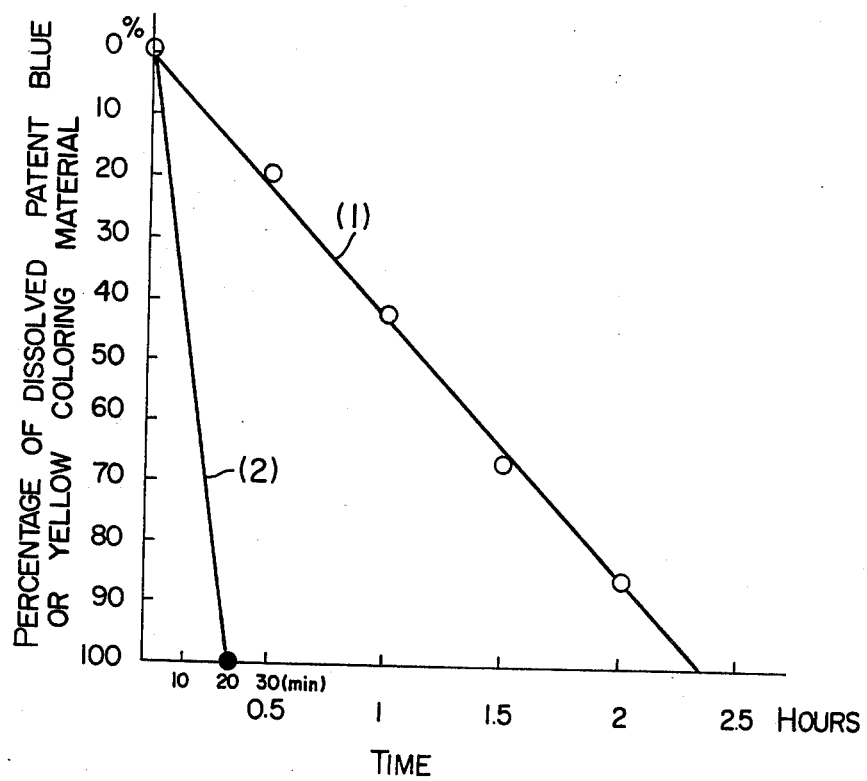
FIG. 1 shows relation between the dissolution rate of the present buccal tablet and the buccal V tablet used as control.

An object of this invention is to provide a pharmaceutical preparation for oral cavity administration, comprising a pharmacologically active agent, a pharmaceutical carrier, and PANA, and a method of making same.

Other objects and advantages of this invention will become apparent from the following description.

Known pharmaceutical preparations for oral cavity administration include buccal tablet, sulbingual tablet, ointment, etc. Of these, buccal tablet and sublingual tablet are pharmaceutical preparations intended for a systemic effect and manifest their full advantage in the case of those drugs such as sex hormones and antiinflammatory enzymes which on oral administration may possibly be decomposed in the digestive tract and the liver, resulting in decreased drug effect. These tablets are placed between the cheek and gingival or under the tongue and allowed to dissolve slowly. The drugs absorbed through the oral mucous membrane enter directly, through not the portal circulation but the systemic circulation. An advantage of these tablets is in the efficient absorption of the drug, because the drug is not decomposed by the liver. However, if the disintegration and dissolution of the tablet are too rapid, the object of such a way of administration is not achieved. The tablet should be prepared so that it may gradually disintegrate or dissolve in the mouth over a period of more than one hour, but actually there is not available a satisfactory preparation.

In order to retard disintegration of the above-said preparations, the following trails have heretofore been made without successful results as a preparation for oral cavity administration:

1. To add larger amounts of a binder, without employing a disintegrant such as starch;
2. to add a large amount of hydrophobic lubricant such as magnesium stearate; and
3. to coat the tablet with a water-repellant substance such as wax or paraffin. On the other hand, as a pharmaceutical preparation for use at a wet site such as oral cavity, there was offered an ointment made by kneading a greasy ointment base together with a hydrophobic macromolecular gum such as gelatin, sodium salt of carboxymethylcellulose, acacia, or pectin to impart to the ointment stickiness and suitable affinity to the wet site (i.e. U.S. Pat. No. 3,029,188). The resulting preparation, however, is not satisfactory in adhesion and dissolves too rapidly to meet the requirement.

As a result of extensive investigations to find a novel preparation for oral cavity administration, in which the above-said defects had been overcome, the present inventors found that when a proper quantity of PANA is incorporated in the base for a preparation for oral cavity administration, the PANA first absorbs water and adheres strongly to the local site, then swells and dissolves gradually at the site over a long period of time, while releasing the medicinal agent substantially uniformly: Based on this finding the present invention has been accomplished.

It has been known that PANA is generally used as (1) a thickening agent or a flocculant, (2) an age-resister for breads, cakes, and vermicelli, (3) a stabilizer for Worcester sauces and catchups, and (4.) a dispersant for ice creams, fruit juices, and beers (see, for example, "Commentary to Official Compendium for Food Additives", 2nd Ed., published by Kimbara Publishing Co., June 30, 1968). It is also known that PANA is effective as a preventive against gastric ulcer of domestic animals (Japanese Patent Application Laid-open No. 75,370/73). However, it has been entirely unknown that PANA may be used as a base for a preparation for oral cavity administration, as is the case with this invention, and that the preparation obtained adheres firmly to the local site and dissolves gradually over a long period of time, while releasing suitable amounts of the medicinal agent.

The PANA used in this invention can be any of those for use as a food additive and its molecular weight, though not critical, is preferably about 185,000 to about 8,500,000 (the intrinsic viscosity is 0.4 to 1.1 [g/dl], as measured in 2N-NaOH at 30° C). The amount to be added is 10 to 60% by weight based on total weight of the preparation.

The pharmacologically active agent suitable for administration as buccal tablet, sublingual tablet, etc., according to this invention and intended to enter directly systemic circulation include steroid hormones; proteins such as antiinflammatory enzymes and callicrein; peptides such as insulin, gastrins, secretin, pepstatin, and leupeptin; nitriate esters such as nitroglycerin and erythrityl tetranitrate; isoproterenol, and methacholine.

The substances suitable for administration as oral ointments and intended to stay in oral cavity for a long period, exhibiting continued local effect, include antiinflammatory steroids; antibiotic bactericides such as leucomycin and fradiomycin; lysozyme for alveolar pyorrhea therapy, dextrinase for preventing teeth from decaying, and local anesthetics.

The pharmaceutical carriers used in the present preparation are, as mentioned later, customary excipients, ointment bases, lubricants, and binders.

As mentioned below in detail, the method of making the present preparation comprises mixing a pharmacologically active agent with a pharmaceutical carrier, and PANA, and treating the resulting mixture in a conventional manner (tabletting or kneading) to obtain pharmaceutical preparations such as buccal tablet, sublingual tablet, and ointment.

In preparing a sublingual tablet or buccal tablet, PANA is used in an amount of 10 to 60% based on total weight of the preparation, depending on the prescription amount and the purpose for administration. To the PANA are added 80 to 10% based on total weight of the preparation of a pharmaceutical carrier and, if necessary, suitable amounts of binder, lubricant, colorant, and flavoring agent.

Pharmaceutical carriers to be used are those microcrystalline cellulose, mannitol, anhydrous lactose, crystalline lactose, spray-dried lactose, sorbitol, anhydrous calcium phosphate, and amylose which are available commercially in the form ready for use as direct compression excipients. There is no harm to use, if necessary, granules or fine granules obtained by adding 1 to 5% by weight of a binder such as polyvinylpyrrolidone, acacia, or gelatin in the form of solution to a saccharide excipient such as powdered lactose or powdered sucrose in the form of preformed granule or fine granule generally known as semi-direct compression excipient or a mixture of such an excipient with other water-insoluble excipients, then granulating the resulting mixture, drying, and screening.

Suitable lubricants are customary magnesium stearate, calcium stearate, talc, Sterotex (Trademark for a nonionic surface active agent manufactured by Monsanto Chemical Co., U.S.A.), and the like, which are generally used. The amount of a lubricant to be used is 0.5 to 2% by weight based on the total weight of the preparation.

In preparing a tablet, a thoroughly blended mixture of PANA with a direct or semidirect compression excipient may be directly compressed into tablets by means of a singlepunch tablet machine or a rotary tablet machine. It is also possible, without causing any trouble, to adopt a method whereby a mixture of components is wet-granulated by use of an organic solvent or the like and then forming into tablets. As stated above, PANA may be directly compressed into tablet. Even finely powdered PANA passing through a 250-mesh screen has desirable flow characteristics and even a formulation containing 60% by weight based on the preparation of PANA may be compressed into tablets without showing any significant fluctuation in weight.

The suitable flavoring agent to be added, if necessary, to modify the taste is an organic acid such as citric acid, tartaric acid, or fumaric acid, because a sour taste is generally preferred. The addition of 1 to 2% of flavoring agent based on total weight of the preparation is sufficient. When the sweet taste is insufficient, it is preferable to add saccharine, a synthetic sweetner, or glycyrrhizin, a natural sweetner. The amount of a sweetner to be added is preferably 1% or less based on total amount of the preparation. As for the colorant, it is preferable to add a lake pigment for food in an amount of about 0.1% based on total weight of the preparation. The flavoring agent to be added to modify the aroma is a natural or synthetic perfume and is used in an amount not exceeding 3% based on total amount of the preparation.

In preparing an ointment, the ointment base to be used is white petrolatum, polyethylene glycol; a mixture of beeswax with a vegetable oil such as peanut oil or purified sesame oil; or Plastibase (a compatible mixture of polyethylene and liquid paraffin; trademark for Squibb Co.). Further, if necessary, there are used nonionic surface active agents such as polyoxyethylene fatty acid esters, polyoxyethylene higher alcohol ethers, polyoxyethylene sorbitan fatty acid esters, and glyceryl fatty acid monoesters and additives such as anhydrous lanolin, cholesterol, squalene, and cetyl alcohol.

To 90 to 50% by weight of the ointment base of the above-mentioned combination, are added 10 to 50% by weight of PANA, depending upon the nature of pharmaceutically active agent which is used in an amount of 10 to 0.05% by weight.

Quite different from conventional buccal tablets, sublingual tablets, and ointments, the pharmaceutical preparation obtained as mentioned above does not interfere with conversation, smoking, and drinking of beverages and can stay in oral cavity for 1 to 8 hours in ordinary daily life. Moreover, owing to distinguished dispersing powder of PANA, the greasy base is also dispersed so that there is produced only very slight feeling of foreign body in oral cavity and, hence, the patients have no urge to crunch and swallow the preparation. Accordingly, the present preparation does not stimulate excessive salivation, which causes swallowing of the pharmacologically active agent dissolved in saliva to reach digestive tract. Further, the present preparation has other advantages in that it does not interfere with false teeth and has little chance of entering the trachea while the partients are asleep.

In the foregoing, mention has been made of making a specific pharmaceutical preparation having good adhesiveness by use of PANA. Distinguished features of the present preparation are illustrated below with reference to Experimental Examples.

Experimental Example 1: Beaker method for dissolution test.

I. Preparation of sample.

Sample No. 1 Buccal tablet according to this invention: A mixture was prepared from 30 g of PANA (passed through 250 mesh screen), 66 g of anhydrous lactose, 3 g of Patent Blue (4′,4″-bisdiethylaminotriphenylcarbinol-2,4-disulfonic acid), and 1 g of magnesium stearate. Using flat face punch, 6 mm in diameter, the mixture was compressed into tablets, each having a weight of 90 mg and a hardness (Erweka hardness tester) of 3 kg.

Sample No. 2 Ointment according to this invention: The ointment was prepared by kneading 48.5 g of PANA (passed through 250 mesh screen), 3 g of Patent Blue, and 48.5 g of white petrolatum.

Sample No. 3 Buccal V tablet of LEDERLE (JAPAN) LTD. (for control): This tablet was flat face bevel edge shaped, 10.5 mm in diameter, 3.5 mm in thickness, 330 mg in weight, and 6–7 kg in hardness, containing 10,000 units of streptokinase and 2,500 units of streptodornase.

Sample No. 4 Ointment (for control): Prepared by kneading together 48.5 g of finely powdered gelatin, 3 g of Patent Blue, and 48.5 g of white petrolatum.

II. Testing procedure.

Testing was carried out in accordance with the method of John H. Wood et al. [Journal of Pharmaceutical Science, 53, 877–881 (1964)].

The acculately weighed sample was fixed on the inner wall of a 500 ml beaker. In the case of tablet, the present preparation was fixed by pressing the moistened sample against the inner wall of the beaker, while the buccal tablet used as control was fixed by means of an adhesive, because it has no adhering property by itself. In the case of ointment, the sample was applied by means of a spatula to the wall so that 4 cm$^2$ of coated area may be produced. Then, 500 ml of water at 37° C. was introduced in the beaker and stirring was started, the rate of stirring being 300 r.p.m. At suitable intervals, each 25 ml of sample solution was withdrawn from the beaker and replenished with equal amount of water to keep the volume of extraction medium unchanged.

The sample solution was diluted to a suitable concentration to obtain a test solution. Absorbance at 638 m$\mu$ of the test solution was measured by means of Hitachi spectrophotometer type 124. The Patent Blue content of 1 ml of the test solution was determined from an analytical curve and multiplied by the dilution ratio to obtain the eluted amount. Since the maximum absorbance of a yellow coloring material in buccal V tablet was 430 m$\mu$, 5 tablets were fixed on the beaker wall in order to obtain a sample solution of measurable concentration.

III Test results.

1. As for buccal tablet.

The results of comparative tests on the present buccal tablet (1) and the buccal V tablet (2) used as control were as shown in FIG. 1. In FIG. 1, percentage of dissolved Patent Blue or a yellow coloring material (ordinate) was plotted against time (abscissa). As is seen from FIG. 1, the buccal V tablet dissolved completely in 20 minutes so that the absorbance was not measured, whereas the present buccal tablet (1) did not become detached under agitation at 300 r.p.m. owing to its strong adhesion and the swollen PANA in paste form covered the tablet, releasing Patent Blue gradually and almost linearly with time until dissolution has been completed in 2.5 hours.

2. As for ointment.

Figure 2:
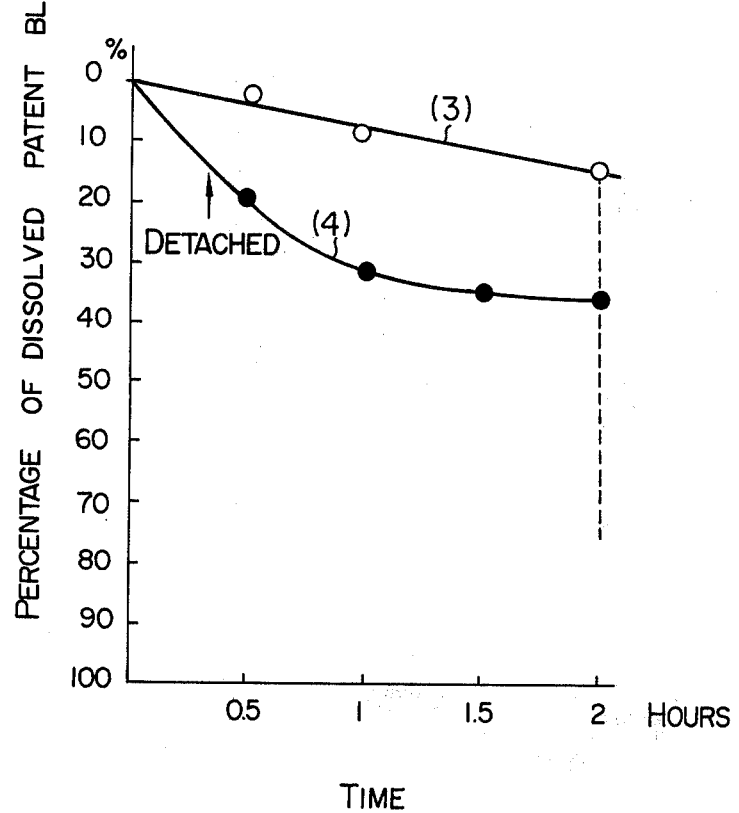
FIGS. 2 and 3 show relations between the dissolution rate as well as detachment times of the present ointment and an ointment used as control. In FIGS. (1) is a curve relating to the present buccal tablet, (2) to control buccal V tablet, (3) and (5) to the present ointment, and (4) and (6) to control ointment, respectively.

The results of comparative tests on the present ointment (3) and the ointment (4) used as control were as shown in FIG. 2. In FIG. 2, percentage of dissolved Patent Blue (ordinate) was plotted against time (abscissa). As is seen from FIG. 2, adhesion of the present preparation was outstanding, did not become deteched after two hours, and with swelling of PANA Patent Blue dissolved gradually and almost linearly with time. To the contrary, the control ointment became detached in about 20 minutes. Dissolution tendencies were as shown in FIG. 2. It is presumable that the ointment used as control might be unable to achieve its intended object, because owing to its weak adhesion to the oral mucosa, the ointment would become detached from the mucosa and possibly be swallowed.

Experimental Example 2: Dissolution test by using esophageal mucosa of dog.

I. Preparation of sample.

The same ointment as used in Experimental Example 1 was used.

II. Testing procedure.

A piece of esophageal mucous membrane of dog, 2.7 cm$^2$ in area, was fixed onto a rubber pad, 4 cm$^2$ in area. The accurately weighed sample of ointment (about 500 mg) was fixed onto the central part of the mucous membrane and placed on the bottom of a beaker filled with 500 ml of a sodium chloride saline solution (37° C) and stirring was effected by means of a small stirrer for testing dissolution at 150 r.p.m. At definite intervals, each 10 ml of sample solution was withdrawn and tested for dissolution of Patent Blue in the same manner as in Experimental Example 1.

III. Test results.

Figure 3:
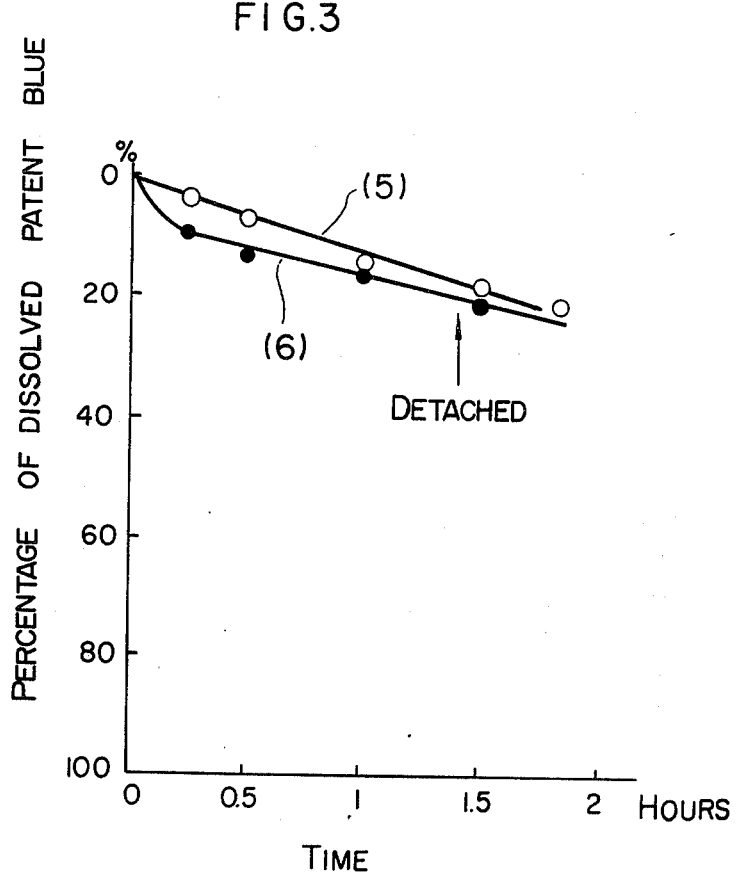

The results of tests on the present ointment (5) and the ointment used as control (6) were as shown in FIG. 3. As is apparent from FIG. 3, the control ointment became detached in 20 minutes in contrast to 180 minutes in the case of the present ointment. It was confirmed that not only the present ointment is superior to the control in adhesion, but also it releases Patent Blue linearly with the lapse of time.

Experimental Example 3. Dissolution test in human oral cavity.

I. Sample (ointment).

An ointment (the present preparation) prepared in the same manner as the sample No. 2 in Experimental Example 1 and an ointment (control) prepared in the same manner as the sample No. 4 were used.

II. Testing procedure.

Accurately weighed amounts (about 0.1 g each) of the sample of the present preparation and the control sample were applied to separate sites between the inside of lower lip and the gingiva of front teeth of two volunteers (A and B). After 30 minutes (during this period the two volunteers continued their daily activities), each ointment remained on the applied site was scraped off and its Patent Blue content was measured. The percentage retention of Patent Blue was calculated based on the Patent Blue content of the initial sample.

III. Test results.

The test results obtained were as shown in Table 1.

Table 1.

| | Percentage retention in oral cavity. | | |
| --- | --- | --- | --- |
| | A | B | Mean |
| The present preparation | 95.0% | 94.5% | 95.0% |
| Control | 61.1% | 55.7% | 58.4% |

As is apparent from the results shown in Table 1, in 30 minutes after application, about 40% of Patent Blue was dissolved from the control sample, whereas only 5% was dissolved from the present preparation, indicating the same tendencies as in Experimental Examples 1 and 2.

In administering the present preparations for oral cavity to a patient, although depending on conditions of patient and affected part, the intended object may certainly be achieved generally with a daily dose of about 3 buccal or sublingual tablets or about 100 mg of ointment for each affected site.

PANA in the present preparation will not show other effects than its intended purpose of increasing adhesion and retarding, by swelling, the dissolution of the drug, because PANA dissolves gradually over a long period of time and the absolute dosage is quite small.

The invention is illustrated below in detail with reference to Examples, but the invention is never limited thereto.

EXAMPLE 1

A thoroughly blended mixture comprising 50 g of PANA (passed through 250 mesh screen), 2 g of chlorophenylamine maleate, 1 g of magnesium stearate, and 47 g of anhydrous lactose was compressed by means of a direct tabletting machine into buccal tablets, each having a weight of 100 mg, a diameter of 7 mm, and a hardness of 3 kg.

EXAMPLE 2

To a thoroughly blended mixture of 30 g of PANA (passed through a 250 mesh screen) and 2 g of lidocaine, was added 68 g of white petrolatum in small portions. The resulting mixture was thoroughly kneaded to obtain an ointment.

EXAMPLE 3

To a thoroughly blended mixture comprising 50 g of PANA (passed through a 250 mesh screen), 1 g of a (1 : 1) mixture of methanesulfonates of dihydroergocornine and dihydroergocrystine, 20 g of microcrystalline cellulose, and 68.0 g of anhydrous lactose, was added 1 g of magnesium stearate. The resulting mixture was thoroughly blended and compressed by means of a direct tabletting machine into sublingual tablets, each having a weight of 160 mg, a diameter of 8 mm, and a hardness of 4 kg.

EXAMPLE 4

A mixture of 30 g of PANA (passed through a 250 mesh screen), 70 g of Plastibase ®, and 1500 mg of bleomycin hydrochloride was thoroughly blended to obtain an ointment having a potency of 15 mg of bleomycin hydrochloride per gram.

What is claimed is:

1. A pharmaceutical preparation for oral cavity administration comprising 10 to 60% by weight of sodium polyacrylate, 90 to 10% by weight of a pharmaceutical carrier selected from the group consisting of an excipient and ointment, and 50 to 0.05% by weight of a pharmacologically active agent.

2. A pharmaceutical preparation for oral cavity administration according to claim 1, wherein the sodium polyacrylate has an average molecular weight of 185,000 to 8,500,000.

3. A pharmaceutical preparation for oral cavity administration according to claim 1, wherein the excipient is microcrystalline cellulose, mannitol, crystalline lactose, spray-dried lactose, sorbitol, anhydrous calcium phosphate, amylose, powdered lactose, or powdered sucrose.

4. A pharmaceutical preparation for oral cavity administration according to claim 1, wherein the ointment base is white petrolatum, polyethylene glycol, a compatible mixture of peanut oil or purified sesame oil with beeswax, or a compatible mixture of polyethylene and liquid paraffin.

5. A pharmaceutical preparation for oral cavity administration according to claim 1, wherein the pharmacologically active agent is selected from the group consisting of a steroid hormone, an antiinflammatory steroid, an antiinflammatory enzyme, callicrein, a peptide, a nitrate ester, isoproterenol, methacholine, an antibiotic, a lysozyme, dextrinase, and a local anesthetic.

6. A pharmaceutical preparation for oral cavity administration according to claim 1, wherein the said pharmaceutical is selected from the group consisting of a buccal tablet, a sublingual tablet, and an ointment.

7. A pharmaceutical preparation for oral cavity administration according to claim 1, wherein the pharmaceutical preparation comprising 10 to 60% by weight of sodium polyacrylate, 80 to 10% by weight of an excipient and 50 to 0.05% by weight of a pharmacologically active agent is a tablet selected from the group consisting of a buccal tablet and a sublingual tablet.

8. A pharmaceutical preparation for oral cavity administration according to claim 1, wherein the pharmaceutical preparation comprising 10 to 50% by weight of sodium polyacrylate, 90 to 40% by weight of an ointment base, and 10 to 0.05% by weight of a pharmacologically active agent is an ointment.

* * * * *